United States Patent [19]

Lussier

[11] Patent Number: 5,130,545
[45] Date of Patent: Jul. 14, 1992

[54] VIDEO IMAGING PLANT MANAGEMENT SYSTEM

[76] Inventor: Robert R. Lussier, 1 Piper Rd., Lexington, Mass. 02173

[21] Appl. No.: 681,189

[22] Filed: Apr. 5, 1991

[51] Int. Cl.$^5$ .......................................... G01N 21/64
[52] U.S. Cl. .............................. 250/458.1; 250/459.1
[58] Field of Search ............... 250/458.1, 459.1, 461.2; 356/317, 417

[56] References Cited

U.S. PATENT DOCUMENTS 4,650,336 3/1987 Moll ..................................... 356/417
5,001,859 3/1991 Sprung .................................. 47/17

Primary Examiner—Carolyn E. Fields
Attorney, Agent, or Firm—Iandiorio & Dingman

[57] ABSTRACT

A video imaging plant management system that determines plant photosynthetic activity and productivity which provides a light source to a plant being analyzed, detects infrared fluorescence emissions from the plant under the light, resolves the plant fluorescence emission over time, and calculates the fluorescence emission decay time from peak to steady state values to provide data indicative of the plant health. Physiological parameters such as plant area and volume are measured over time to monitor productivity. Ambient monitoring of water vapor and carbon dioxide may also be used for an overall plant growth management system.

31 Claims, 2 Drawing Sheets

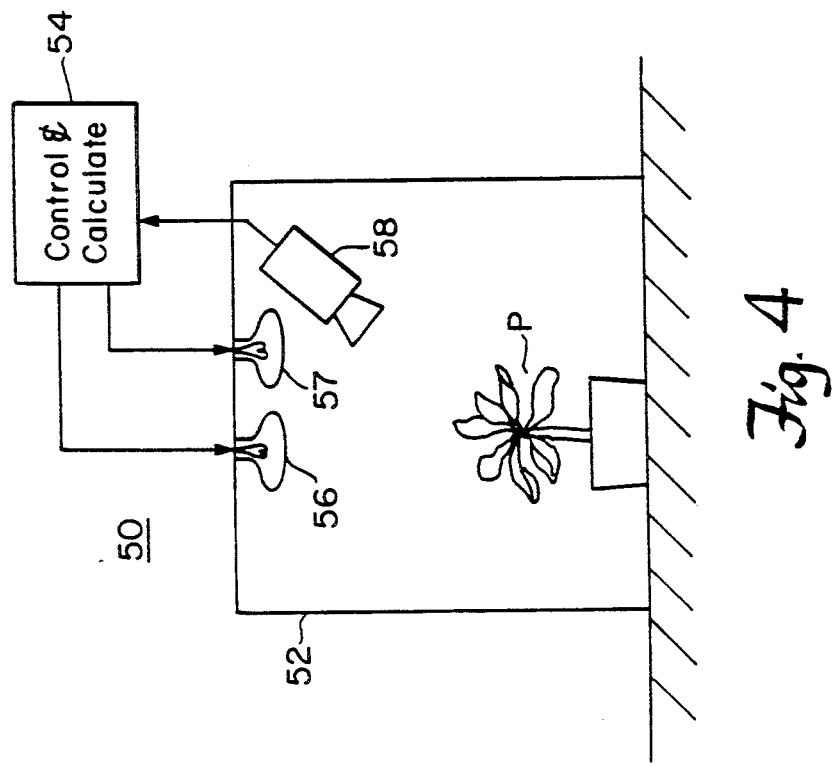
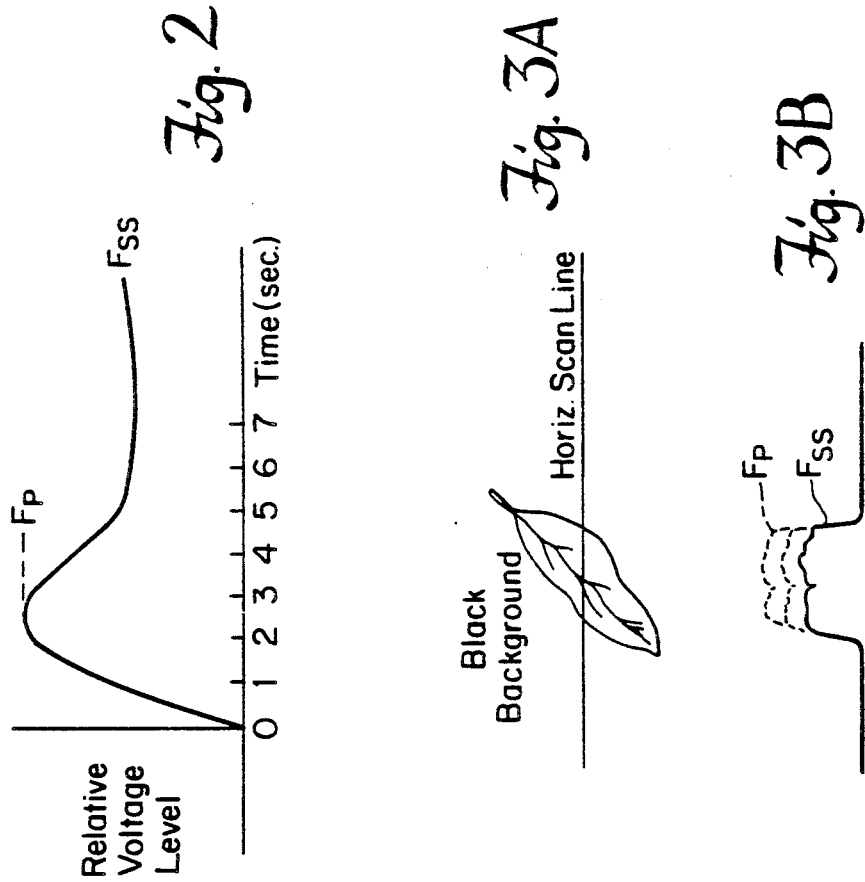

VIDEO IMAGING PLANT MANAGEMENT SYSTEM

FIELD OF INVENTION

This invention relates to plant stress detection using video imagery and a video imaging plant management system which allows the professional to closely monitor plant health.

BACKGROUND OF INVENTION

Professional growers desire to optimize plant growth management in order to achieve productive objectives. For example, to optimize growth and conserve resources, growers would ideally like to know if the temperature, light level, nutrient and water levels, and disease and insect populations are at desirable levels. To date, however, no system has existed which could quickly and accurately monitor the variables required to supply such information.

There have been a number of attempts to measure plant stress using the Kautsky effect in order to provide additional information for the grower. The traditional Kautsky apparatus, as described in U.S. Pat. No. 4,084,905, measures the induced chlorophyll fluorescence as an indicator of the photosynthetic mechanism. The above-described as well as U.S. Pat. Nos. 4,650,336, 4,804,850, and 4,942,303 describe various types of Kautsky measuring devices. These devices, however, are test instruments not adapted for field use and not able to provide the information required for overall plant management. For example, these devices typically measure only a spot area on a single leaf, invasively or destructively examine a leaf or small pieces of leaves; they accordingly cannot measure whole plants or areas of plants. Further, these devices typically measure the base line fluorescence, peak fluorescence, and steady state fluorescence to define a variable fluorescence indicative of photosynthetic activity. These measurements, however, only provide some of the information necessary for an overall plant management system.

SUMMARY OF INVENTION

It is therefore an object of this invention to provide a video imaging plant management system which provides management and diagnostic data that quantifies plant growth, plant productivity and plant health which can be used by the commercial grower to optimize plant growth.

It is a further object of this invention to provide such a system which can be used to monitor a part of a plant, an entire plant, or a greenhouse or field of plants as desired.

It is a further object of this invention to provide such a system which monitors temperature stress in plants.

It is a further object of this invention to provide such a system which monitors plant light stress.

It is a further object of this invention to provide such a system which monitors plant drought stress.

It is a further object of this invention to provide such a system which monitors plants for responses to chemicals such as fertilizers, pesticides, herbicides and growth regulators.

It is a further object of this invention to provide such a system which monitors plant viral, bacterial and fungal disease.

It is a further object of this invention to provide such a system which monitors insect populations.

It is a further object of this invention to provide such a system which monitors the plant live weight, yield and growth rate.

This invention results from the realization that a plant management system may be provided that measures plant stress and plant productivity on-line in the greenhouse and field by measuring the plant's emission energy as plant fluorescence emission over time and the emission decay time from peak to steady state values in order to indicate stress brought on by any number of stress-inducing factors in the plant growth environment, and by making other spectral measurements that supply information indicative of the plant's overall productivity.

This invention features a video imaging plant management system and method which includes means for providing an illuminating light source to a plant being analyzed, means for detecting infrared fluorescence emissions from the plant, means for resolving the plant fluorescence emission over time, and means for calculating the fluorescence emission decay time from peak to steady state values for providing data indicative of the plant health.

The absorbed light energy may be provided with a steady blue light source along with a means such as a shutter for temporarily interrupting the light to partially dark adapt the plant. Preferably, the blue light is provided within the range of 350 to 550 nm, as may be accomplished with a mercury lamp or a white light and low pass blue filter for passing the light within the prescribed range.

The fluorescence emission may be detected with a silicon charge-coupled device (CCD) detector having a matrix of light sensing pixels, or a line scanner with a row of pixels. Further included may be one or more narrow band filters or a high-pass band filter for passing desired infrared band(s) to the CCD, for example 680 nm for plant fluorescence measurements, and higher wavelengths for ambient detection of carbon dioxide and water vapor.

The system may also detect the plant's infrared ambient-light emission level with the CCD and subtract that infrared level from the infrared ambient and fluorescence emission level under ambient and blue light to determine the value due only to fluorescence.

Preferably, the system and method determines the plant fluorescence emission peak value, the steady state value, and the decay time or time to reach steady state from the peak. The system may examine part of, or a single scan line of the CCD, a number of lines, or the entire array. There may further be included means for digitizing the pixel outputs and storing the digitized outputs. The system may also calculate physiological parameters such as the approximate plant area and plant volume. The system may further include means for shielding the plant from ambient light, and means for determining ambient conditions such as the relative ambient water vapor level by measuring the light absorption level from the ambient water vapor, and/or the relative ambient carbon dioxide level by measuring the light absorption from carbon dioxide.

DISCLOSURE OF PREFERRED EMBODIMENT

Other objects, features and advantages will occur to those skilled in the art from the following description of a preferred embodiment and the accompanying drawings, in which:

FIG. 2 is a plot of a typical plant fluorescence emission over time using the system of this invention;

FIGS. 3A and 3B are simplified schematic diagrams of a single horizontal scan line using the system of this invention across a single leaf and the change in the output over time as the leaf is subjected to visible blue light showing the decay from the peak to the steady state value; and FIG. 4 is a schematic diagram of the system of this invention in use measuring stress on an entire plant.

Figure 1:
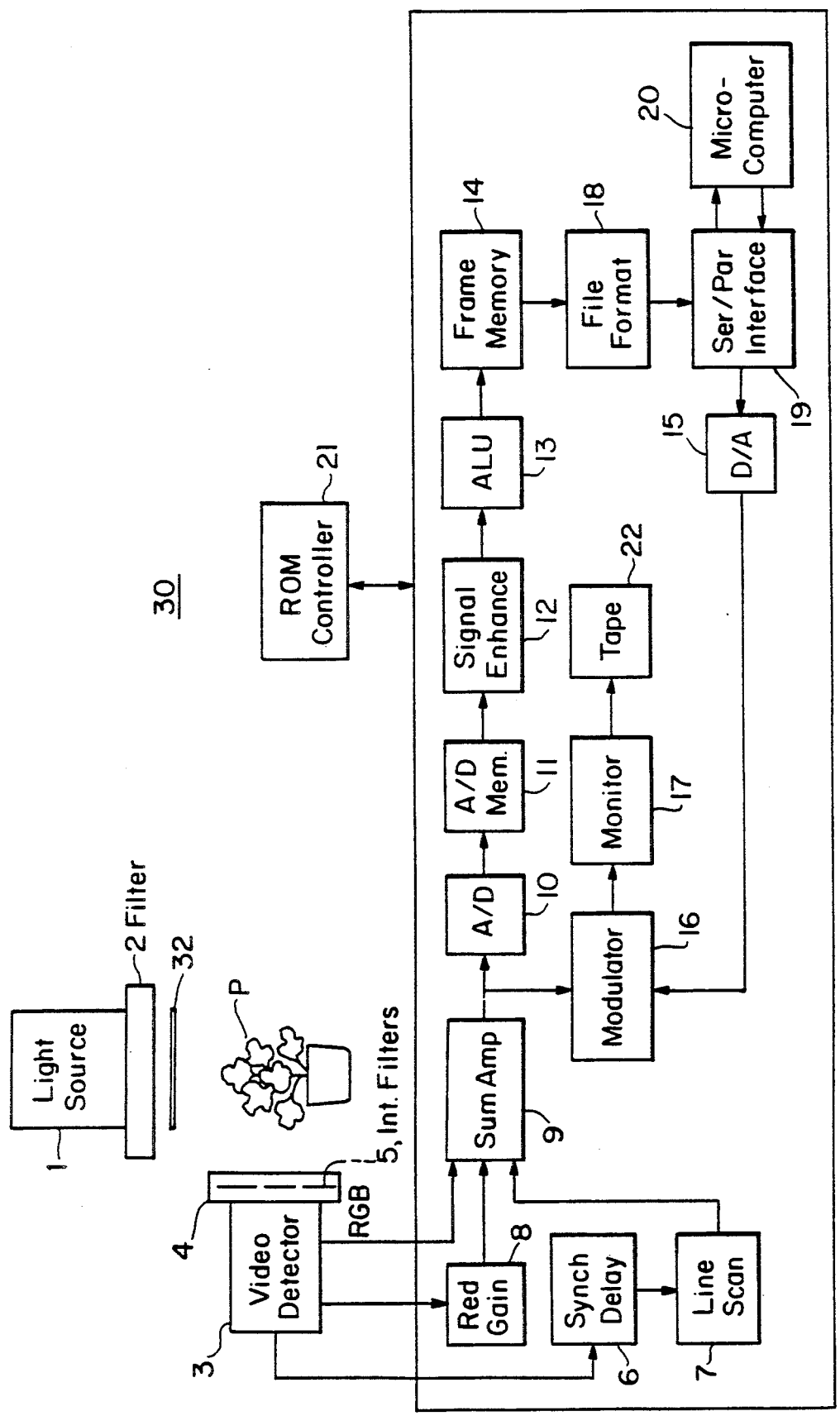
FIG. 1 is a schematic block diagram of a video imaging plant management system according to this invention.

This invention features a video imaging plant management system which provides visible light to a plant being analyzed, the light preferably a blue-green light within the range of 400 to 550 nanometers (nm) along with some means for detecting the infrared fluorescence emission from the plant, preferably accomplished with a charge-couple device (CCD) camera having a matrix of light sensing pixels along with a narrow band filter passing only a narrow infrared band to the CCD camera preferably approximately 680 nm. The system further includes means for resolving plant fluorescence emission over time, preferably by sensing the peak and steady state fluorescence levels, along with means for calculating the fluorescence emission decay time from the peak to the steady state value to provide data indicative of the plant health.

The operation of the system is as follows. Blue-green light (400–550 nm) is a constant light source that illuminates and is absorbed by the plant. A blue filter is used to prevent any red light from the lamp spectra that would conflict with the measured fluorescence in the 680 nm red region. The constant light source will cause a normal fluorescent signal component, Fss, to be emitted from the plant. If the plant is suffering a temporary stress (caused by environment or chemical) the emitted Fss will be greater than a normal plant. If the plant has suffered permanent damage due to disease or chill temperature, Fss will be less than a normal plant. When the light source is shuttered, to prevent light for at least 30 seconds, and then unshuttered to instantaneously illuminate the plant, there is caused an instantaneous increase in absorbed energy levels. Fss will increase to a peak value Fp, and then decay in time Td to the Fss level. When compared to normal plant levels, the values Fp, Fss, and Td define the type of plant stress (temporary and permanent) and are the basis for defining the plant management system of this invention.

There is shown in FIG. 1 video imaging plant management system 30 according to this invention. System 30 includes light source 1, blue filter 2, and light shutter 32 for illuminating plant P in visible light. Preferably, light source 1 is a mercury lamp such as a GTE Sylvania H37KB. Filter 2 may be a band pass filter which passes blue light in the range of approximately 400 to 550 nm. Such a blue filter can be constructed using a glass enclosure with a solution containing 1M cupric sulfate ($CuSO_4$) with a light path of at least 1.5 cm so that any red light emitted from the lamp and heater element which would be reflected off the surface of the leaves of plant P is not supplied to the system. In use in ambient light, there will be reflectance from plant P. However, the system is able to account for such reflectance to measure only the fluorescence as described below. Shutter 32 is preferably employed to alternately block and pass light source 1 to provide control over the plant irradiation with the blue light so that there is no need to use the flash arrangements of some of the existing Kautsky effect devices. The device may use a collimated and/or converging lens, not shown, to parallel or focus the blue light upon the plant as desired. Various lens can be used at the camera to measure part or all of a single leaf, a number of leaves, an entire plant, or a number of adjacent plants as desired to provide measurements of plant stress or measurements of the plant's environment to accomplish an overall plant management system.

Plant P absorbs the blue light and emits some of the light energy as fluorescence at 680 nanometers. This fluorescence is detected by video detector 3 which is preferably a charge coupled device (CCD) having an array of pixels for capturing the emission over an area determined by the size of the array and the lens system used. In one embodiment, detector 3 has mounted thereon a rotating disc 4 that contains one or more narrow band interference filters 5 so that various narrow bands in the emission spectrum can be sampled. One filter is centered at 680 nm and other filters may be centered at other wavelengths corresponding to spectral phenomena being monitored. For example, the system may be used to monitor ambient carbon dioxide and water vapor concentration by detecting absorption at known maxima in the CCD detection range. Video detector 3 may be accomplished with a Texas Instruments Detector TC225 Containing 285×285 active pixels. Larger area arrays may be used to increase the image resolution.

The management system can operate in two modes. The first uses an isolating light box that only allows the blue light source to illuminate the plant. In this mode, the fluorescent parameters Fp, Fss, and Td can be measured directly.

In the second mode, operation is at ambient light levels in the greenhouse or field. Since practically the total plant irradiance at 680 nm is the reflective component plus the fluorescent signal, the system must subtract the reflective component from the total incident light to leave the fluorescent signal. Again the incident blue light source is used but only to enhance the measurable fluorescent signal component. Again shuttering the light source will cause the transient response and the values of Fp, Fss, and Td will continue to measure the effect of plant stress.

To accomplish this the system may measure at 680 nm the plant emission under ambient light, where the reflective component is much greater than the fluorescent signal. This measurement may be stored and a second measurement, under the light source plus ambient light, may be taken. Under control of the Controller 21, the system may subtract the stored ambient signal from the ambient plus fluorescent signal in arithmetic logic unit 13 to obtain a signal due to fluorescence only. The subtraction can occur pixel by pixel in the line scan values or group of lines that are imaged from the plant.

A second method used to measure fluorescence in ambient light is to measure the green light at 550 nm. Since green light is not absorbed by the plant chlorophyll pigments, the measured value will be the reflective component. This value can be subtracted from the total measured value at 680 nm. However, In vivo, there is some green light absorption by plant enzymes. The first method is preferred as it offers the opportunity to compare and calibrate measurements to the enclosed light box fluorescence measurement.

Typically, either the RGB output from detector 3 or the amplified red channel output from amplifier 8 is supplied to summing amplifier 9. The horizontal synch signal from video detector 3 may be applied to synch delay circuit 6 so that line scan selector 7 may be used to take the output of a single line scan, a group of lines or the whole image as desired. The summed signal is digitized in circuit 10 and stored in memory 11. Electronic enhancement circuit 12 cancels noise-signal artifacts and stores the result. ALU 13 subtracts the stored ambient scan from the incoming light plus ambient scan and the resultant output is stored in frame memory 14. Frame memory 14 thus captures the output comprising one or more scan lines or the entire CCD array resulting from the fluorescence emission at 680 nm. The output of frame memory 14 may then be formatted for file storage in circuit 18, output by the serial/parallel interface 19 and transferred to microcomputer 20. The microcomputer stores the image as a formatted file. Using application software programs, the microcomputer will link and store associated text and data with the image files to accomplish the management objectives.

The user or operator may also reverse the information direction and call from the microcomputer, stored imagery and data, to be displayed on the video monitor. Under control of controller 21, the computer-stored imagery and text may be returned to monitor 17 for viewing. First it is analog restored by D/A 15. Modulator 16 may then supply the analog signal to monitor 17 for viewing, and/or tape storage 22 for long term storage. The plant image may also be displayed by taking the signal directly from summing amp 9 as shown.

Those skilled in the field will understand that the data obtained by the above-described measurement techniques may be evaluated by numerous known techniques, each of which maintains the spirit of the invention. For example software may be used to implement the digital processing techniques of A/D memory 11, signal enhance 12, ALU 13, memory 14, format 18 and interface 19, and operate directly from microcomputer 20.

FIG. 2 illustrates schematically an output over time from monitor 17 for a leaf or plant. As can be seen, for a typically healthy plant the 680 nm fluorescent signal, depicted as a relative voltage level that is similar to an oscilloscope trace, rises from 0 for a partially dark adapted plant (shutter closed for 20 to 30 seconds and no ambient light) up to a peak value in approximately 2 seconds and then decays to a steady state value over the next several seconds. In experimental measurements, it has been found that the time to reach peak may occur from one to two seconds and the decay time may vary approximately from two to four seconds beyond the peak. The system of this invention is able to determine, save and output the peak fluorescence, steady state fluorescence, and the fluorescence decay time, or the time it takes for the signal to decay from peak to the steady state value. Each of these variables is important in providing data required for overall plant management.

A more illustrative example of the output of the system for a single scan line across a leaf is illustrated in FIGS. 3A and 3B. In this example, a leaf is being scanned across a horizontal scan line or single row of pixels of the CCD, or with a line scanner, in which the leaf is placed against a black background (black cardboard placed behind the leaf) to further distinguish the leaf signal from the background signal. The black reference may be used as a zero-emission standard in calibrating the measurements on the monitor or as data input to the computer. As shown in FIG. 3B, the output rises to a peak level and then decays to a steady state level at which it remains indefinitely. This figure also illustrates that the fluorescence values vary somewhat across the width of the leaf, and decrease at the leaf veins. The system may average the signal and create a time averaged output such as shown in FIG. 2.

The system of this invention thus may use line-scan and raster scan video to electronically and visually measure the fluorescent and visible and other spectral signatures of plants. The system uses measurements of the fluorescence with no incident light, peak fluorescence, steady state fluorescence and decay time from peak to steady state to measure and discriminate plant stresses. It has been found that for temporary stress affecting the plant's electron transport system, such as that which may be caused by chemical, drought or light stress, the steady state and peak fluorescence values are greater than that in normal plants; disease and low temperature freezing causes permanent damage which decreases the steady state and peak fluorescence values.

In using a silicon detector having the ability to detect at wavelengths of up to approximately 1,000 nanometers, the system may be used at 680 nm to measure these fluorescence values, and also may be used to measure at absorption maxima of water and carbon dioxide to measure the absolute or relative concentration of ambient water vapor or carbon dioxide in order to provide data for allowing the grower to better manage the plant environment. For example, if the carbon dioxide level is too low or depleted, the system may be enabled to warn the grower to open greenhouse vents, may be enabled to automatically open vents with electric motors, or to start $CO_2$ generators. The ambient water vapor levels may be used as an indicator of plant drought stress in more exactly managing irrigation schedules.

The system may also employ other detectors such as a lead sulfide detector having a greater detection range than a silicon detector to include up to 5,000 nanometers with appropriate filtering to measure these and other variables such as leaf temperature.

This system may also be used to monitor insect population by looking at a leaf and subtracting from the captured leaf image the leaf color to leave an image created by insects. This image would be a number of dots—one for each insect area. The computer with scan/image algorithms using an average area per insect could then "count" or determine the insects as a measure of insect area and population using ALU 13, FIG. 1, for insecticide management.

FIG. 4 depicts schematically measurement system 58 used within enclosure 52 which blocks ambient light to measure fluorescence emissions from plant P with blue light source 56 and control and calculate circuitry 54. White light 57, such as a tungsten halogen lamp such as used in film projectors, may be used to capture plant images so that the image, plant area, volume and other physiological parameters such as color, bloom area, and stalk size may be measured, stored and compared to previous values for plant quality control. When the system is used in ambient conditions as described above, ambient light may provide the white light source. The system may thus be used to measure the cross-sectional area of a plant, its pigmentation and coloring, its live weight based on leaf area or volume, the number of blooms, fruit and branches, and the plant growth rate by measuring the plant size over time. For example, a single plant taken from the crop population could be imaged and measured periodically for growth rate and yield as indicative of that of the entire crop for plant management purposes.

Plant area may be measured by scanning, with an appropriate lens and the camera approximately 3 to 5 feet from the plant, to present a total image of the plant. A standard block or scale should also be present so as to be captured with the imagery. The standard may be a black rectangle, 2 inches by 1 inch or greater, to be readily recognizable in the image. Image software in the computer can calculate the image area (width × height) and determine the perspective direction or camera angle. Correlating to scale the width-height values, the plant area may then be calculated through pixel count. Similar algorithms may be used to define plant volume.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A video imaging plant management system, comprising:
   means for providing blue light to a plant being analyzed;
   video detector means for detecting infrared fluorescence emission from the plant;
   means for resolving the plant fluorescence emission over time; and
   means for calculating the fluorescence emission decay time from peak to steady state values for providing data indicative of the plant health.

2. The video imaging plant management system of claim 1 in which said means for providing blue light includes a steady light source.

3. The video imaging plant management system of claim 2 in which said means for providing blue light further includes means for temporarily interrupting said light source to partially dark adapt the plant for measuring the transient infrared fluorescent emission level.

4. The video imaging plant management system of claim 3 in which said means for interrupting includes a light shutter.

5. The video imaging plant management system of claim 1 in which said blue light is within the range of 350 to 550 nm.

6. The video imaging plant management system of claim 1 in which said means for providing blue light includes a low pass light filter for only passing light within the range of 400 to 550 nm.

7. The video imaging plant of claim 1 in which said means for detecting includes a silicon charge-coupled device (CCD) having a matrix array of light-sensing pixels.

8. The video imaging plant management system of claim 7 in which said means for detecting further includes a bandpass filter for passing an infrared band including 680 nm to said CCD.

9. The video imaging plant of claim 8 in which said means for resolving includes means for examining the output of at least some of the pixels of one line of pixels in said array.

10. The video imaging plant management system of claim 9 further including means for digitizing said pixel outputs.

11. The video imaging plant management system of claim 10 in which said means for calculating includes means for storing the digitized outputs.

12. The video imaging plant management system of claim 9 further including means for calculating the plant leaf or plant area.

13. The video imaging plant management system of claim 12 in which said means for calculating the plant leaf of plant area includes means for storing the output of the entire CCD pixel array.

14. The video imaging plant management system of claim 12 further including means for calculating the plant volume.

15. The video imaging plant management system of claim 1 further including means for illuminating the plant being analyzed with ambient or white light to allow measurement of plant physiological parameters for plant quality analysis to provide an overall plant productivity measurement system.

16. The video imaging plant management system of claim 15 further including means for detecting the plant emissions from the ambient or white light.

17. The video imaging plant management system of claim 16 in which said means for resolving includes means for subtracting the ambient light plant emission from the ambient plus blue light plant emission to resolve said infrared fluorescence emission.

18. The video imaging plant management system of claim 1 in which said means for resolving includes means for determining the plant fluorescence emission peak value.

19. The video imaging plant management system of claim 18 in which said means for resolving further includes means for determining the plant fluorescence emission steady state level following said peak value.

20. The video imaging plant management system of claim 19 further including means for resolving changes in peak and steady state fluorescence values for determining temporary or permanent chemical plant stress for chemical level management.

21. The video imaging plant management system of claim 1 further including means for shielding the plant from ambient light.

22. The video imaging plant management system of claim 1 further including means for determining the relative ambient water vapor level.

23. The video imaging plant management system of claim 22 in which said means for determining includes means for measuring the ambient water vapor spectral absorption level.

24. The video imaging plant management system of claim 1 further including means for determining the relative ambient carbon dioxide level.

25. The video imaging plant management system of claim 24 in which said means for determining includes means for measuring the ambient carbon dioxide spectral absorption level.

26. The video imaging plant management system of claim 1 further including means for determining the insect area.

27. The video imaging plant management system of claim 26 further including means, responsive to said means for determining the insect area, for determining the quantity of insects.

28. A video imaging plant management system, comprising:
- a filtered blue-green light source for providing light within the range of 400 to 550 nm to a plant being analyzed;
- a charge-coupled device (CCD) having an array of pixels for detecting infrared fluorescence emission from the plant at approximately 680 nm;
- means for examining the output of at least part of one line of pixels of the CCD array;
- means for determining the fluorescence emission peak value;
- means for resolving the fluorescence emission steady-state level following said peak value; and
- means for calculating the fluorescence emission decay time from peak to steady-state values for providing data indicative of the plant health.

29. The video imaging plant management system of claim 28 further including means for illuminating the plant being analyzed with ambient or white light for measurement of plant physiological parameters for plant quality analysis to provide an overall plant productivity measurement system.

30. A method of managing the productivity of plants, comprising:
- supplying a filtered blue-green light in the range of 400–550 nm to a plant;
- measuring over time the plant fluorescence level at approximately 680 nm;
- resolving from the measured level the peak and steady state fluorescence, and the decay time from peak to steady state as indicative of temporary or permanent plant stress;
- supplying ambient, blue-green, or a white light to the plant for visual analysis; and
- capturing a video image of the plant over time for measurement of plant physiological parameters to provide data indicative of plant growth over time.

31. The method of claim 30 further including measuring the spectral signatures of at least one of ambient water vapor and carbon dioxide for monitoring the plant's ambient conditions.

* * * * *